United States Patent [19]

Rocco

[11] Patent Number: 4,834,702
[45] Date of Patent: May 30, 1989

[54] KIDNEY-URETER CATHETER ASSEMBLY FOR EVACUATION OF CRUMBLED CALCULI

[75] Inventor: Francesco Rocco, Milan, Italy

[73] Assignee: Hoechst Italia Sud SPA, Italy

[21] Appl. No.: 20,482

[22] Filed: Mar. 2, 1987

[30] Foreign Application Priority Data

Mar. 4, 1986 [IT] Italy ................................ 21123/86[U]
Feb. 10, 1987 [IT] Italy ............................... 20790/87[U]

[51] Int. Cl.⁴ ............................................. A61M 25/00
[52] U.S. Cl. ...................................... 604/43; 604/170; 604/250; 251/4
[58] Field of Search ...................... 604/54, 43, 170, 95, 604/280–283, 246, 250, 34, 159, 164, 165; 128/344; 251/9, 10, 4, 7, 117

[56] References Cited

U.S. PATENT DOCUMENTS

| 3,166,819 | 1/1965 | Robbins | 251/4 |
| 3,261,357 | 7/1966 | Roberts et al. | 604/105 |
| 3,698,681 | 10/1972 | Lacey | 251/10 |
| 3,724,461 | 4/1973 | Eisenberg | 251/4 |
| 3,822,052 | 7/1974 | Lange | 251/10 |
| 3,847,370 | 6/1974 | Engelsher | 251/6 |
| 3,942,228 | 3/1976 | Buckman et al. | 251/4 |
| 4,560,378 | 12/1985 | Weiland | 604/187 |
| 4,571,239 | 2/1986 | Heyman | 604/54 |
| 4,581,025 | 4/1986 | Timmermans | 604/264 |
| 4,589,626 | 5/1986 | Kurtz et al. | 251/10 |
| 4,616,652 | 9/1986 | Simpson | 128/344 |
| 4,643,389 | 2/1987 | Elson et al. | 251/10 |
| 4,645,496 | 2/1987 | Oscarsson | 251/117 |
| 4,673,161 | 6/1987 | Flynn et al. | 251/4 |

FOREIGN PATENT DOCUMENTS

| 2161709 | 1/1986 | European Pat. Off. | 604/280 |
| 8200413 | 2/1982 | PCT Int'l Appl. | 604/280 |

Primary Examiner—Stephen C. Pellegrino
Attorney, Agent, or Firm—Darby & Darby

[57] ABSTRACT

A kidney-ureter catheter unit comprises a flexible catheter (2) provided with an introduction end (2a) of truncated conical form close to which radial drainage holes (3) are pierced. Within catheter (2) is slidably engageable a semi-rigid dilator mandrel (4) provided with an introduction end (4a) of truncated conical form and in turn slidably engaged by a semi-rigid guide element (12) having a rounded introduction end (12a). A spring (5) detachably fastens mandrel (4) to catheter (2) in an insertion condition with respect to each other in which the introduction ends (2a, 4a) of catheter (2) and mandrel (4) have the respective generators in alignment, so as to form a continuous frusto-conical surface.

5 Claims, 2 Drawing Sheets

KIDNEY-URETER CATHETER ASSEMBLY FOR EVACUATION OF CRUMBLED CALCULI

FIELD AND BACKGROUND OF THE INVENTION

The present invention relates to a kidney-ureter catheter assembly particularly adapted to evacuate crumbled calculi. More specifically the invention is designed to be used to achieve the drainage of calculus fragments resulting from the destruction of renal calculi through modern techniques using shock waves, ultrasounds or the like.

At the present time calculus fragments obtained as a result of the above therapy are directly evacuated through ureter and urethra. However this solution can give rise to a series of complications because, above all when calculi of great sizes are concerned, the obtained fragments can obstruct ureter owing both to their relatively important dimensions and to the fact that they are numerous.

On the other hand, it is to be noted that at the present state of the art the evacuation of said fragments through drainage cannot be obtained in a satisfactory manner. This is essentially due to the fact that ureter is a very delicate canal and has a very reduced clearance, so that it is almost impossible to introduce catheters or probes of appropriate sizes thereinto without the risk of its tearing.

For the above reasons the modern and advantageous techniques consisting in "bombarding" calculi by means of ultrasounds or the like cannot be used when renal calculi have relatively important sizes.

OBJECTS

It is therefore an object of the present invention to solve the above specified drawbacks by providing a kidney-ureter catheter assembly arranged so that it is easily insertable into urethra and ureter without any risk of tearing the same and adapted to allow calculus fragments to be evacuated even if they have relatively important sizes and are numerous.

A further object of the present invention is to provide a assembly which is convenient to handle and use and adapted to be easily produced by the industries of the sector.

SUMMARY OF THE INVENTION

The foregoing and still further objects which will become more apparent in the following are substantially achieved by a kidney-ureter catheter assembly particularly adapted to evacuate crumbled calculi, comprising:
- a flexible tubular catheter provided with an introduction end substantially of truncated conical form in the vicinity of which at least a drainage hole substantially extending in a radial direction is pierced;
- a semi-rigid dilator mandrel of tubular configuration provided with an introduction end of truncated conical form, said mandrel being longer than the catheter and being slidably engageable within the latter to be brought to an insertion condition in which the introduction end thereof extends beyond the catheter's introduction end; and
- a semi-rigid guide element of cylindrical section exhibiting a rounded introduction end slidably engaging the dilator mandrel.

BRIEF DESCRIPTION OF THE DRAWINGS

Further features and advantages of the invention will become more apparent from the detailed description of a preferred embodiment of a kidney-ureter catheter assembly given hereinafter by way of non-limiting example with reference to the accompanying drawings, in which.

DESCRIPTION OF A PREFERRED EMBODIMENT

Figure 1:
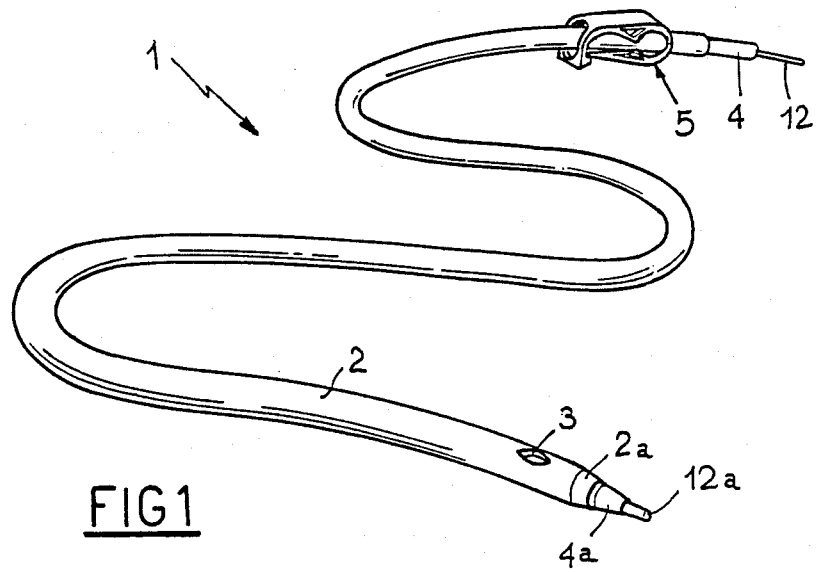
FIG. 1 is a perspective diagrammatic view of the catheter assembly in question.

Referring to the drawings and particularly to FIG. 1, reference numeral 1 globally denotes a kidney-ureter catheter assembly, particularly adapted to evacuate crumbled calculi in accordance with the present invention.

Unit 1 comprises a catheter 2 of suitable length and having a cylindrical tubular section. Catheter 2 is provided with a tapered introduction end 2a substantially of truncated conical form. Close to the introduction end 2a provision is made for one or more substantially radial drainage holes 3. More particularly, two drainage holes 3 are provided which are disposed at diametrically opposed positions spaced apart by a different distance from the introduction end 2a.

Catheter 2 is made of flexible material especially manufactured so that the difference between the catheter outer diameter and the catheter inner diameter may be very small. In addition to the above features, the material of which catheter 2 is made must be soft and biocompatible so that it may stay inside body for a long time without causing any damages.

To this end, catheter 2 can be made for example of a polyvinyl chloride (resin) and low density polyethylene composition to which plasticizers and diluents are added, such as di-2-ethylhexyl-phthalate, epoxy soybean oil, calcium -zinc stearate in epoxy soybean oil, basic zinc (22%) octoate, calcium - zinc stearate in an organic base, glycerol mono-oleate and/or other similar products.

Furthermore the material used for catheter 2 can advantageously be a radiopaque material so that it is possible to check the position thereof within the patient's body by a radiography. This characteristics can be for example achieved by adding the above specified composition of barium sulfate.

Figure 2:
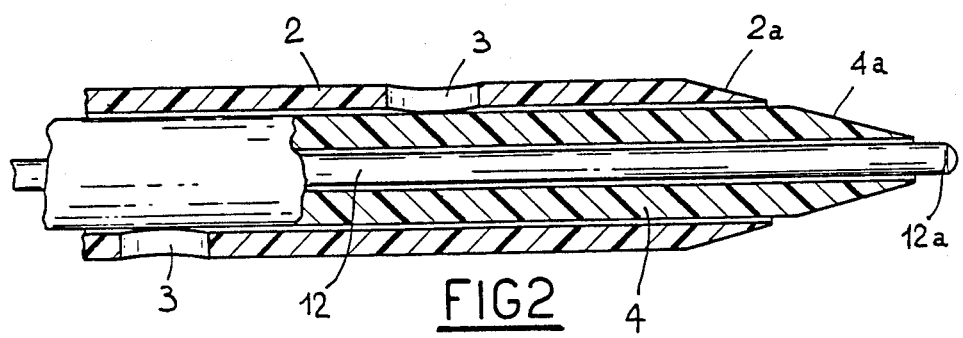
FIG. 2 is an enlarged broken and partly sectional view of the elements composing the catheter assembly according to the invention in the region of the introduction ends thereof.

Assembly 1 also comprises a dilator mandrel 4 of cylindrical tubular section too, provided with an introduction end 4a substantially of truncated conical form. Dilator mandrel 4 is longer than catheter 2 and its outer diameter is slightly smaller than the inner diameter of the catheter so that it can be slidably engaged within the same. In fact said dilator mandrel 4 must be engaged inside catheter so that it may be disposed according to an insertion arrangement allowing the introduction end 4a of mandrel 4 to extend beyond the introduction end 2a of catheter, as shown in FIG. 2. Preferably, in said insertion condition the introduction ends 4a and 2a of mandrel 4 and catheter 2 respectively should have their respective generators substantially aligned so that a substantially continuous frusto-conical surface can be obtained.

Preferably mandrel 4 is made of semi-rigid plastic material which can be made radiopaque too for example by addition of barium sulfate to the material composition.

The mutual positioning of mandrel 4 and catheter 2 according to the above insertion arrangement is advantageously achieved by fastening means preferably consisting of a spring 5 acting upon catheter 2 at the end thereof opposite the introduction end 2a. According to the present invention spring 5 is comprised of substantially parallel first 6 and second 7 fastening portions linked to each other by a spring portion. Fastening portions 6 and 7 are provided with respective facing gripping areas 9 and 10.

Spring 5 also has a clasping portion 11 adjoining the first fastening portion 6 and extending therefrom towards the free end of the fastening portion 7.

A first opening 8a and a second opening 11a are provided in the clasping portion 11 and spring portion 8 respectively, through which openings spring 5 can be slidably engaged on catheter 2 as shown in FIG. 1.

Fastening portions 6 and 7 can be brought from a rest position in which they are spaced apart from each other thereby allowing spring 5 to slide over catheter 2, to an operating condition in which said fastening portions are moved close to each other in such a way that the gripping areas thereof are spaced apart from each other by a maximum distance which however must be shorter than the outer diameter of catheter 2 and bigger than the outer diameter of dilator mandrel 4. Under this condition catheter 2 is squashed against the dilator mandrel 4 surface without causing the latter to be in turn deformed.

Figure 3:
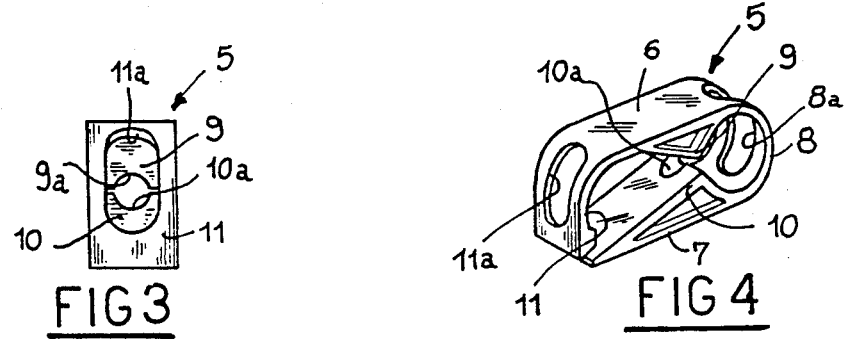
FIG. 3 is a front view on an enlarged scale of a component of the catheter assembly according to the present invention.
Figure 4:
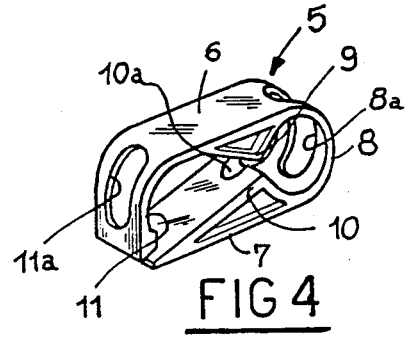
FIG. 4 is a perspective view of the component seen in FIG. 3.

In the embodiment shown it is also advantageously provided for the gripping areas 9 and 10 to have respective hollows of semi-circular configuration. As shown in FIG. 3 in which a front view of spring 5 in its operating condition is seen, said hollows 9a and 10a give rise, under this situation, to a circular opening the diameter of which is smaller than the outer diameter of the catheter and bigger than the outer diameter of the mandrel. The mutual positioning of fastening portions 6 and 7 in their operating condition is maintained, in opposition to the action exerted by the spring portion 8, through the engagement of the free end of the second portion 7 with the clasping portion 11.

The catheter assembly 1 further comprises a semi-rigid guide element 12 of cylindrical section having a diameter slightly smaller than the inner diameter of the dilator mandrel 4. Guide element 12 is intended to slidably house mandrel 4 and is provided with a rounded introduction end 12a disposed on the same side as the introduction ends 4a and 2a previously described, as clearly shown in FIG. 2.

OPERATION

Operation of the catheter assembly according to the invention described above mainly as regards structure, is as follows.

Figure 5:
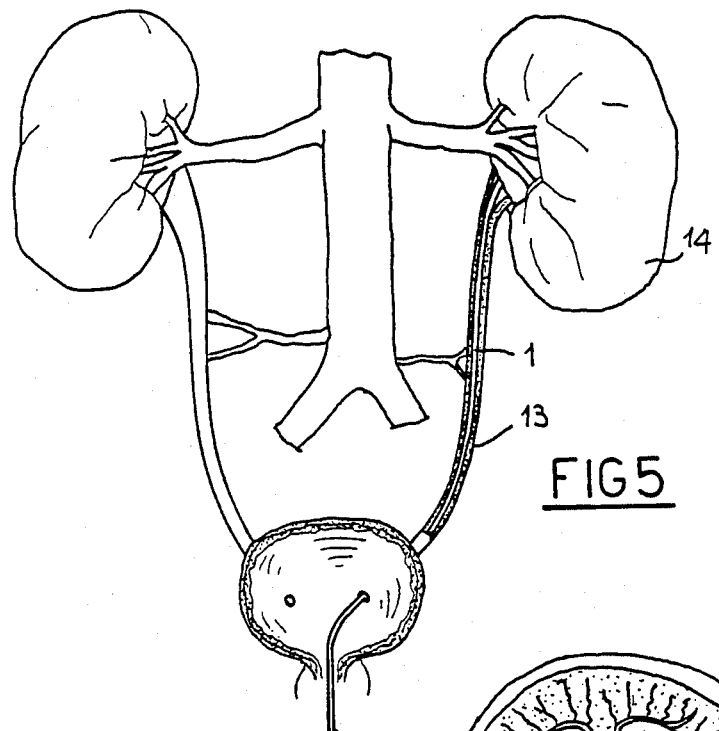
FIG. 5 diagrammatically shows the catheter assembly in question introduced into body through ureter until it reaches the kidney.

First of all guide element 12, starting from its introduction end 12a, is inserted into urethra (not shown) and is then pushed through bladder and ureter, identified by reference numeral 13 in FIG. 5, as far as said end 12a comes close to the kidney identified by reference numeral 14.

Advantageously guide element 12 has a very reduced diameter, so that it can be easily introduced into ureter without tearing the same or causing traumas thereto.

Afterwards dilator mandrel 4 and catheter 2, arranged in an insertion condition and fastened to each other by spring 5 being operative, are caused to slide along guide element 12 which suitably guides them through urethra and ureter until the introduction ends 4a and 2a thereof reach the area where the connection between ureter 13 and kidney 14 takes place. This connection area has been identified by reference numeral 13a in FIG. 6.

It is to be underlined that, as previously said, spring 5 has such structural features that its action on catheter 2 does not cause any deformations on the dilator mandrel 4 so that sliding of the latter along the guide element 12 is not hindered.

Furthermore, the frusto-conical surfaces of introduction ends 4a and 2a when arranged for insertion cause, at the moment of the above specified insertion operation, a gradual dilating of urethra and ureter, without tearing the same or otherwise causing traumas thereto. Once end 2a of catheter 2 has properly reached the connection area 13a as above specified, spring 5 is manually brought to its rest condition and guide element 12 and dilator mandrel 4 are withdrawn from catheter 2.

Figure 6:
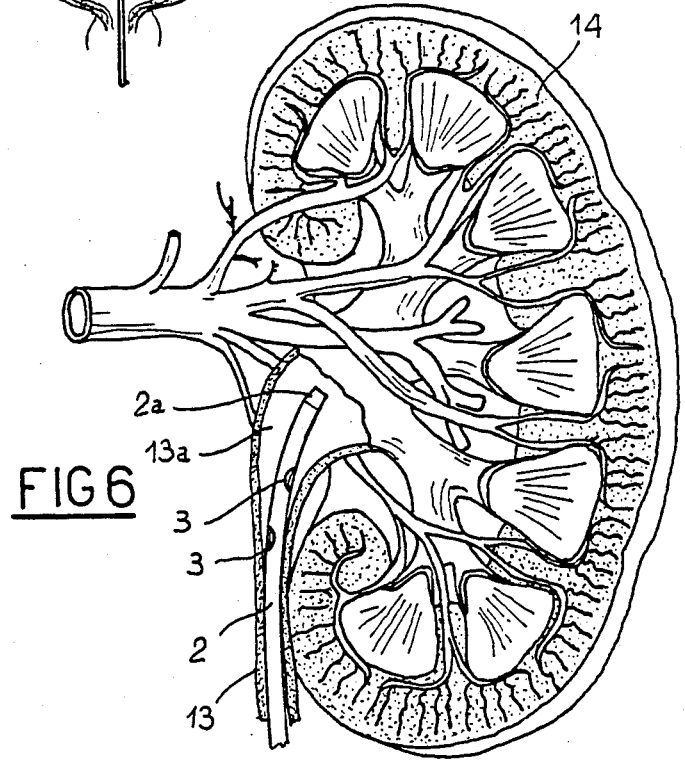
FIG. 6 is a broken sectional view showing the positioning of the catheter being part of the assembly in question, relative to the kidney.

At the end of the above operation catheter 2 has been therefore introduced into urethra and ureter and its end 2a has been situated in the connection area 13a as seen in FIG. 6. Under this situation, the presence of holes 3 allows an easy drainage of calculus fragments after calculi, following an ultrasound therapy, have been crumbled.

It will be recognized that sizes of holes 3 and of the inner diameter of catheter 2 have been advantageously studied so that they may allow for the evacuation of important amounts of fragments even of relatively big dimensions.

The present invention attains the intended purposes. In fact, as clearly apparent from the above description, the catheter assembly being the subject of the present invention can be easily inserted into body through urethra until it reaches the kidney without any risks of tearing the canals through which it is caused to pass or of causing traumas thereto. In addition, as it allows for the evacuation of an important number of calculus fragments which may also have relatively big sizes, said catheter assembly makes it possible to adopt ultrasound-type therapies or the like even when it is necessary to act on big renal calculi.

Furthermore the catheter assembly of the invention has a very simple structure which can be accomplished by the industries of the sector at low prices.

What is claimed is:

1. A kidney-ureter catheter assembly for evacuation of crumbled calculi comprising a semi-rigid guide element having a substantially cylindrical cross-section and a rounded tip at one end thereof for slidable insertion through a urethra and the ureter to place the tip in a vicinity of a kidney;

a semi-rigid intermediate member having a tubular configuration and a first end of a frasto-conical configuration, said guide element being insertable within said intermediate member;

a flexible tubular catheter provided with a second end having a substantially frusto-conical configuration, said intermediate member being slidably insertable into said catheter in such a manner that in an assembled condition said first end of the intermediate member and said second end of the catheter form a substantially continuous surface having a frusto-conical configuration; and fastening means for detachably fastening the catheter to the intermediate member when said elements are inserted into each other in the assembled condition comprising;

a spring element having a first fastening portion provided with a first gripping area;

a second fastening portion having a free end which is substantially parallel to the first fastening portion and having a second gripping area facing the first gripping area;

a spring portion connecting the first and second fastening portions to each other; and a clasping portion extending from the first fastening portion towards the free end of the second fastening portion and engageable with the second fastening portion in a removable manner to hold fastening portions in opposition to the action exerted by the spring portion in an operating condition in which the respective gripping areas are provided with respective hollow parts of a semi-circular cross-section which, in the operative condition, give rise to a circular opening smaller in diameter than an outer diameter of the catheter and larger in diameter than an outer diameter of the intermediate member.

2. The catheter assembly as claimed in claim 1, wherein said catheter is made of radiopaque material.

3. The catheter assembly as claimed in claim 1, wherein said intermediate member is made of radiopaque material.

4. The catheter assembly as claimed in claim 1, wherein said spring is slidably engaged along the catheter through first and second openings situated wihtin the spring portion and the clasping portion respectively.

5. The catheter unit as claimed in claim 1, wherein said gripping areas are spaced apart from each other by a distance shorter than the outer diameter of the catheter and longer than the outer diameter of the intermediate member.

* * * * *